United States Patent [19]

DeFord et al.

[11] 4,283,201

[45] Aug. 11, 1981

[54] METHOD AND APPARATUS SUITABLE FOR REPEATED, ACCURATE CHEMICAL ANALYSES

[75] Inventors: Donald D. DeFord, Glenview, Ill.; Edwin K. Clardy; Edward N. Fuller, both of Bartlesville, Okla.

[73] Assignee: Phillips Petroleum Company, Bartlesville, Okla.

[21] Appl. No.: 90,838

[22] Filed: Nov. 2, 1979

[51] Int. Cl.³ .................... G01N 1/14; G01N 31/08; G01N 31/16; G01N 35/08
[52] U.S. Cl. .................... 23/230 A; 23/230 R; 422/62; 422/75; 422/76; 422/82
[58] Field of Search ............ 23/230 A, 230 R; 422/82, 81, 75, 76, 62

[56] References Cited

U.S. PATENT DOCUMENTS

| | | | |
|---|---|---|---|
| 3,276,843 | 10/1966 | Cooper, Jr. | 23/230 A |
| 3,333,090 | 7/1967 | Neer . | |
| 3,341,299 | 9/1967 | Catravas | 23/230 R |
| 3,625,655 | 12/1971 | Culp et al. | 23/230 A |
| 3,935,097 | 1/1976 | Roof | 210/31 C |
| 4,009,998 | 3/1977 | Benningfield | 23/230 R |
| 4,022,575 | 5/1977 | Hansen | 23/230 R |
| 4,141,687 | 2/1979 | Forrest et al. | 422/82 X |
| 4,151,255 | 4/1979 | Capuano et al. | 422/62 X |

OTHER PUBLICATIONS

Analytica Chimica Acta, 79 (1975) 79–91.
Analytica Chimica Acta, 81 (1976) 371–386.
Analytica Chimica Acta, 79 (1975) 145–157.
Analytica Chimica Acta, 81 (1976) 387–396.
Analytica Chimica Acta, 82 (1976) 137–144.
Analytica Chimica Acta, 87 (1976) 353–363.
Analytica Chimica Acta, (1977) 235–249.
Analytica Chimica Acta, 91 (1977) 87–96.
Analytica Chimica Acta, 91 (1977) 97–106.
Analytical Chemistry, vol. 44, (1) pp. 100–104.
Analytical Chemistry, vol. 45, (4) pp. 782–786.

*Primary Examiner*—Ronald Serwin

[57] ABSTRACT

A continually repeated chemical analysis of a process stream sample is effected by interposing the sample in a flow of titrant, flow of which is interrupted only to permit the interposition of the sample in the line of flow. A holding zone or chamber, e.g. a chromatographic column receives and holds titrant until the interposed sample in the column is titrated. Reaction product eluted from the column is detected.

29 Claims, 4 Drawing Figures

BLOCK DIAGRAM COLUMN TITRATION APPARATUS

BLOCK DIAGRAM COLUMN TITRATION APPARATUS

FIG.2 dv/dt CIRCUIT DIAGRAM

METHOD AND APPARATUS SUITABLE FOR REPEATED, ACCURATE CHEMICAL ANALYSES

BRIEF SUMMARY OF THE INVENTION

A method and apparatus are disclosed for providing continually repeated or sequential on-line chemical analyses of a process stream or the like. Sample titration is effected utilizing a holding zone or column, e.g. a chromatographic column and a titrant, of known concentration and flow rate as a sample carrier with the holding zone or column functioning to retain a known or metered and injected sample for a time sufficient to enable quantitative reaction thereof with the titrant flowing through said column continuously except when the injected sample, in effect sharply defined slug, is flowing into and reacting in said zone, thus creating a titrant "vacancy" in the zone or column effluent which is detected and can be recorded. This vacancy can be differentially detected and recorded to provide a time period thereof which is linearly and quantitatively related to said sample period. A quantitative sample analysis is achieved by means including a packed column functioning as a mixing chamber into which alternate increments of a suitable reagent and sample are made. A solvent carrier can be used to receive and to convey the reagent and sample to the holding or mixing zone or chamber wherein said reagent is retained on said packing for a time sufficient to be overtaken by said sample and to be reacted therewith resulting in a reaction product eluted to a suitable detection means.

DETAILED DESCRIPTION

Figure 1:
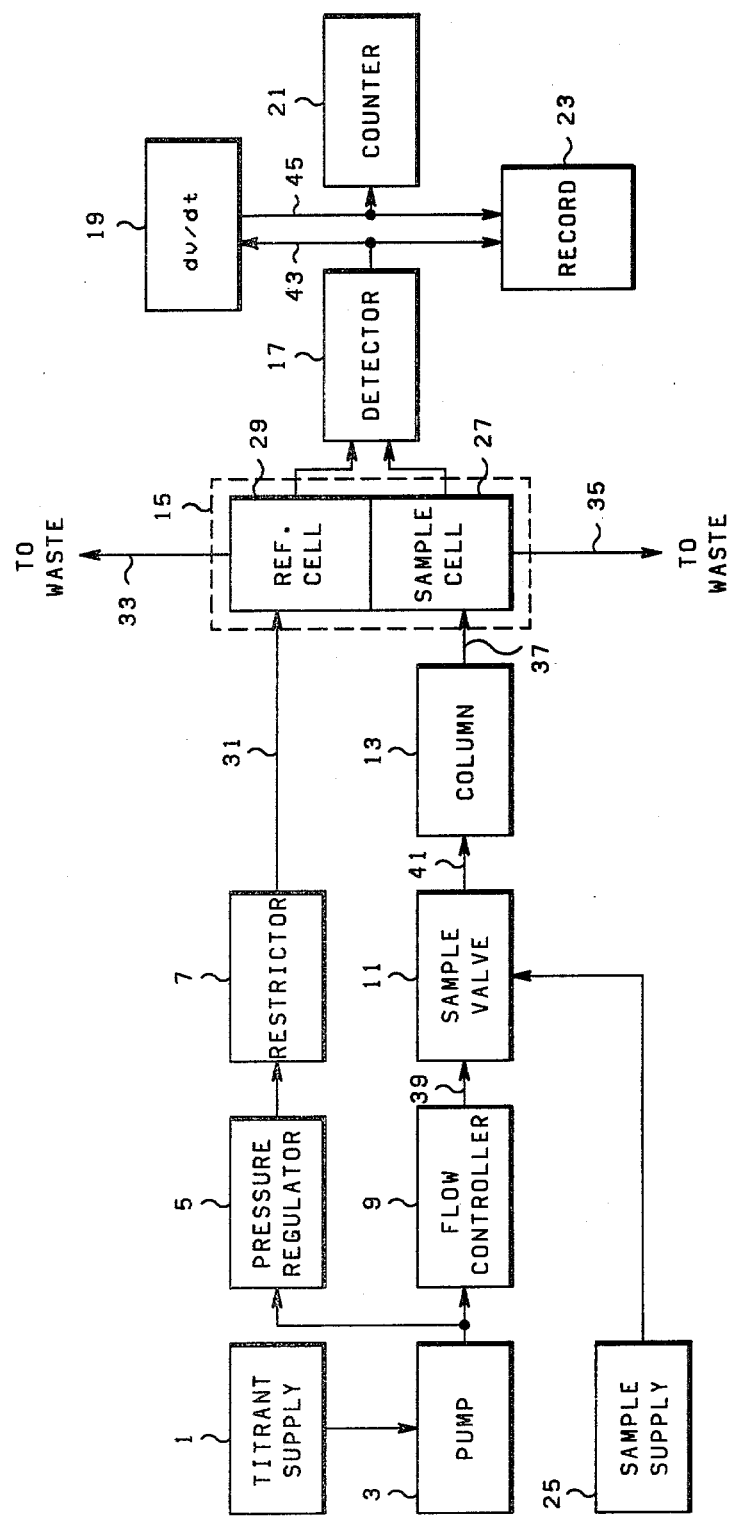
FIG. 1 is a block diagram and schematically shows interconnection of various components which operatively make up the titration means of the present invention.

This invention relates to a method suitable for repeatedly and continually performing a chemical analysis e.g. a titration. It also relates to apparati for carrying out the method of the invention.

In one of its aspects, the invention relates to a continually operable chemical analysis method in which repeatedly there can be removed from an operation a predetermined quantity of a sample for analysis as by titration. In a more specific aspect of the invention it relates to a method and to apparati for carrying out such repeated analyses.

In one of its concepts, the invention provides a method for effecting a repeated chemical analysis of a process stream which comprises establishing a first flow of a stream of a first reactant into a reaction zone, retaining in said zone first reactant entering said zone, continuing said first flow until there is established in said zone a quantity of first reactant sufficient to effect in said zone a reaction or titration therewith and with a second reactant when the latter has entered said zone, the momentarily discontinuing said first flow and simultaneously initiating a second flow of a predetermined quantity of said second reactant into said zone, then immediately upon the termination of said second flow, recommencing said first flow into said reaction zone, removing reaction product from said reaction zone, and determining at least one of the amount and nature of reaction product thus formed and removed from said zone.

In another of its concepts, the invention said first flow is of a reagent and said second flow is of a sample to be analyzed. In a further concept of the invention the flow of reagent and/or sample is aided with a solvent or diluent. In a still further concept of the invention, the reaction product is employed to alter a signal from a photometer and/or a conductivity cell. In another concept of the invention, a property of the reaction product is determined over a period of time in an analyzing zone emitting a signal representative of the first reactant when it is alone in said analyzing zone and of the reaction product when it is in the analyzing zone and there is employed a second stream of said first reactant in a parallel analyzing zone emitting a signal representative of said first reactant, the signals received from the analyzing zones are compared and recorded with respect to at least the period of time during which the signals are different.

In a further concept still, the invention provides a method, as herein described, wherein a first stream of a titrant or sample is continuously caused to flow into and through a reference conductivity cell, a second stream of sample or titrant is caused to flow into a chromatographic or equivalent column or zone that to retain said titrant until it is reacted with a known amount of said sample, flow of said second stream of titrant is abruptly discontinued while simultaneously there is injected a flow of said known amount of sample, the flow being abruptly initiated and substituted for a same amount of said titrant flowing into said column or zone; flow of second stream of said titrant is immediately resumed after flow of said known amount of sample has been terminated, the effluent from said column or zone is caused continuously to flow to and through a second conductivity cell; the conductivities of the respective flows in said cell are determined and caused to emit signals respectively representative of the natures of the fluids in said cells, and wherein said signals are then combined to yield a final signal which is recorded with respect to time elapsing during generation of said signal.

In a further concept of the invention, the signals are detected during the time when these are different and measured the difference in them being caused to initiate operation of a counter and to continue operation of said counter while the signals are different and to stop said counter when the signals have again become the same.

A further concept of the invention provides an embodiment in which a comparator and a D flip-flop are used, as further described herein below, to initiate and to stop the operation of said counter. In a still further concept of the invention the output of the detector, as described, is supplied to the input of a differentiator, the output of which is supplied to the first input of said comparator.

In another of its concepts, the invention provides an apparatus for repeatedly chemically analyzing a sample from a process stream, the apparatus comprising in combination a reagent or titrant supplying means, a sample supplying means, a means for receiving and holding one of said reagent and sample, until both are in said means for holding and have reacted therein, a flow control means adapted to alternately supply said reagent and a predetermined quantity of said sample to, into and through said holding means, means to detect the difference in a property of the effluent from said witholding means when said effluent is constituted by reagent at one time and by reaction product at another, and means to record a signal representataive of the change or difference in said property while said difference is extant. In a still further concept of the invention, in an embodiment thereof, now preferred, the said holding means comprises a chromatographic column. In another concept of the invention, now preferred especially for reaction products which readily cause changes in light being transmitted, there is employed a photometer to detect differences in the properties herein discussed.

In another concept of the invention, it provides means to supply flow of a reagent at a predetermined rate to and through a conductivity cell, means to flow the effluent from a holding means, i.e. reaction zone or chromatographic column, to and through another conductivity cell, means to provide and obtain from each of said cells a signal representative of the respective conductivites of fluid in said cells, and means to detect and to combine said signals and to record a signal resulting from the combined signals with respect to the passing of time.

Various methods and apparati have been suggested to perform chemical analyses.

The following publications, which are incorporated herein by reference, are to an extent of interest to a more full presentation and consequent understanding of the present invention in its various aspects, concepts, and objects.

Automation of chemical analyses, based on continuous flow measurement, is described in Flow Injection Analysis, Part II. Ultra-fast Determination of Phosphorus in Plant Material by Continuous Flow Spectrophotometry, J. Ruzicka and J. W. B. Stewart, Analytica Chimica Acta, 79(1975)79–91. The method described utilizes rapid injection of an aqueous sample into a continuously moving carrier stream of a reagent. The injected sample forms a zone which is then transported toward a detector, which continuously records the absorbents or changes the electrode potential, etc. The method employs a continuously moving carrier stream which, apparently, is not interrupted during the injection of the aqueous sample.

In Analytica Chimica Acta, 79(1975)145–157, J. Ruzicka and E. H. Hansen in Flow Injection Analysis, Part I. A New Concept of Fast Continuous Flow Analysis, on page 146 described continuous flow analyzers in which the samples are successively aspirated from their individual containers into a tube through which they move until the whole analysis is completed. The samples become a part of a continuously moving stream into which at predetermined points, reagents are added at fixed flow rates. The process stream finally flows through the cell of a spectrophotometer in which the quantitative measurement is executed and the signal continuously recorded.

In Analytica Chimica Acta, 81(1976)371–386, J. W. B. Stewart, J. Ruzicka, H. H. Bergamin Filho and E. A. Zagatto in Flow Injection Analysis Part III. Comparison of Continuous Flow Spectrophotometry and Potentiometry for the Rapid Determination of the Total Nitrogen Content in Plant Digests, described on page 371 a new approach based on rapid injection of the sample solution into a carrier stream of a reagent. The injected samples are said to form a well defined zone which is then transported towards a detector. During this transport, the sample solution is mixed with the carrier stream and reacts with its components to form a species which is quantitatively measured in a flow-through detector. The authors state that as long as the chemical reactions are fast enough the carrier stream does not need to be segmented by air, because the carry-over can effectively be prevented by keeping the conduit to the analyzer shorter by creating a turbulent flow.

Other articles dealing with flow injection analysis or continuous flow analysis, wherein a sample zone is injected into a moving stream or discussing continuous titration technique for titrations in continuously flowing solutions are the following:

Analytica Chimica Acta, 81(1976)387–396, J. Ruzicka, J. W. B. Stewart and E. A. Zagatto, Flow Injection Analysis Part IV. Stream Sample Splitting and its Application to the Continuous Spectrophotometric Determination of Chloride in Brackish Waters Analytica Chimica Acta, 82(1976)137–144, J. W. B. Stewart and J. Ruzicka, Flow Injection Analysis Part V. Simultaneous Determinaton of Nitrogen and Phosphorus in Acid Digests of Plant Material with a Single Spectrophotometer Analytica Chimica Acta, 87(1976)353–363, Elo H. Hansen and Jaromir Ruzicka, Flow Injection Analysis Part VI. The Determination of Phosphate and Chloride in Blood Serum by Dialysis and Sample Dilution Analytica Chimica Acta, (1977)235–249, J. Ruzicka, E. H. Hansen and H. Mosbaek, Flow Injection Analysis, Part IX. A New Approach to Continuous Flow Titrations Analytica Chimica Acta, 91(1977)87–96, G. Nagy, Zs. Feher, K. Toth and E. Pungor, A Novel Titration Technique for the Analysis of Streamed Samples—the Triangle-Programmed Titration Technique Analytica Chimica Acta, 91(1977)97–106, G. Nagy and Zs. Feher, A Novel Titration Technique for the Analysis of Streamed Samples—the Triangle-Programmed Titration Technique.

The following articles are included as references, generally, to vacancy chromatography.

In Some Aspects of Liquid-Solid Vacancy Chromatography, by R. P. W. Scott, C. G. Scott, and Paul Kucera, Analytical Chemistry, Vol. 44 (1) pages 100–104, there is discussed vacancy chromatography using a liquid-solid system to evaluate differences in composition between a circulating mobile phase and an injected sample. In the article it is stated that a reference mixture is pumped continuously through the column with the columm effluent being recycled. Also, conversely, the reaction mixture can be cycled and the reference samples injected.

In Analytical Chemistry Vol. 45 (4) pages 782–786, in Sample Vacancy Chromatography and Catalysis, E. S. G. Phillips, and C. R. McIlwrick, the application of sample vacancy chromatography is discussed as being especially convenient for the study of reactions carried out in columns. Gas-chromatographic examples are given of their application to catalytic reactions and of their relation to stopped-flow reaction chromatography.

U.S. Pat. No. 3,333,090 July 25, 1967 H. M. Neer relates to application of an analyzer using digital integration techniques and the principles of chromatography. FIG. 1 of the drawing of the patent shows the use of a differentiator, pulse shapers, etc.

Figure 2:
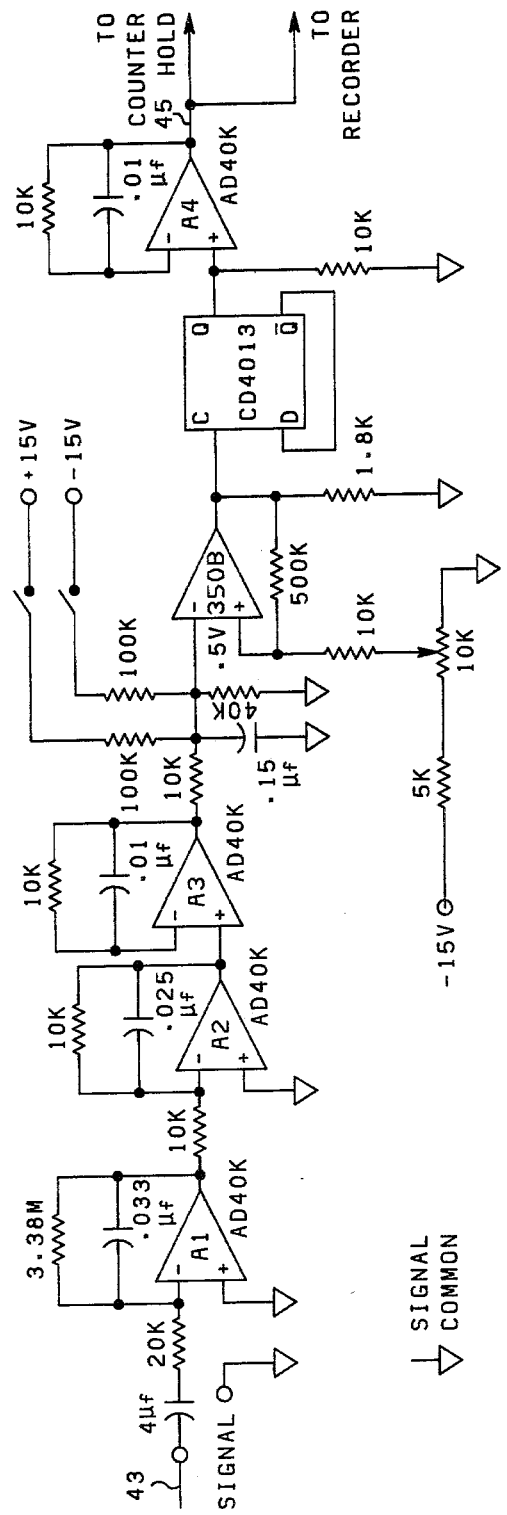
FIG. 2 is a schematic diagram of a dv/dt circuit for use with the invention.

U.S. Pat. No. 3,935,097, Jan. 27, 1976 Lewis V. Roof shows the application of a chromatographic column in continuous control of a hydrofluoric acid alkylation unit and a detector, obtaining the tracing as shown in FIG. 2.

U.S. Pat. No. 4,009,998, Mar. 1, 1977 L. V. Benningfield, Jr., discloses the use of a mixing device 16 which can be packed with particulate material, a conductivity detector and a recorder adapted to measure the concentration of acid in a fluid stream.

U.S. Pat. No. 4,022,575, May 10, 1977 describes an automatic chemical analyzer in which a continuous flow analysis of a liquid sample in a carrier is effected by injecting a sample into said stream as a discrete volume at or upstream from a station at which flow is turbulent.

The present invention provides accurate, readily readable recordings. It is desirable to avoid diffusion of the sample or reagent until the instant reaction in the reaction zone or chromatographic column or equivalent occurs. This is to avoid or substantially reduce, if not eliminate tailing or sample spreading.

It is an object of this invention to provide a method for effecting a chemical analysis. It is another object of this invention to provide an apparatus for effecting a chemical analysis. It is a further object of this invention to provide a method to effect continually, repeated chemical analyses. Another object is to provide an apparatus for effecting continually repeated analyses. It is a further object of the invention to provide a method for effecting a reaction of at least two reactants in a manner such that repeated samples of a reactant can be sequentially analyzed with a high degree of accuracy. It is a further object of the invention to provide an apparatus with which such analyses of high degree of accuracy can be effected. A further object of the invention is to provide method and apparatus making use of chromatograhic analysis, employing a chromatographic (resin-filled) column to effect a reaction or titration, obtaining a so-called "titrant vacancy". It is a further object of the invention to provide a method and apparatus providing accurate and readily measurable recordings of a "titrant vacancy".

A still further object of the invention is to so arrange apparatus components as to permit effective use of a chromatographic column in producing a titrant vacancy. Another object of the invention is to provide an electrically operated detection means, including a differentiator, a counter and a recorder in a manner such that a titrant vacancy is automatically graphed. A further object of the invention is to so arrange apparatus components, including a chromatographic column, a detector and a recorder that chemical reactant or titration as evidence by light reflection or transmission can be accurately graphed.

Other aspects, concepts, and objects of the invention are apparent from a study of this disclosure, the drawings and the appended claims.

According to the present invention, as set out herein a concept thereof includes discontinuing the flow of a reactant or reagent while there is placed or interposed into the line of flow an accurately metered amount of a sample or other reactant or reagent. The interruption and interposing operations are virtually simultaneously effected to create an interface between the rear face or end of the interrupted reactant and the front face of the interposed material when the interpositioning is begun and a similar accurate interface between the rear end or face of the interposed, say, sample and the front face of the first reactant, flow of which has been interrupted, when said flow thereof is resumed.

Importantly, as described in connection with an embodiment of this invention in which a chromatographic column or equivalent is employed, it will be seen that the interface, first created, will be quite sharp, well-defined, and will reach the column at a well defined moment for reaction therein and that there will have been experienced very little sample spreading over a large volume of the reactant or reagent first introduced before reaction ensues in the column. This will result, according to the invention, in a well defined start as well as a well defined end of a titrant vacancy as discussed herein in connection with FIG. 3.

Although chemical analysis procedures, including titrations, are routinely conducted within the confines of industrial laboratories, such analysis procedures are not readily adaptable for use with automatic process control systems because of the difficulty of automating conventional laboratory apparatus such as pipets, burettes, titration vessels with stirrers, etc. Prior attempts at resolving this problem provide means which function to a degree which is somewhat less desirable. For example, some known types of equipment take sequential samples of a solution that is to be analyzed for some component, mixes the sample with an appropriate reagent to carry out some chemical reaction that is specific for the component to be determined, and finally passes the mixture through a "detector" that measures the concentration of the reaction product; thus providing a readout that is proportional to the concentration of the component in the original sample. In designing an instrument of this type, careful design is required to insure thorough mixing of sample and reagent but simultaneously insure minimum sample spreading in the conduits. These two requirements are difficult to realize because a certain amount of turbulence is necessary for proper mixing. However, such turbulence results in considerable sample spreading over a rather large volume. One known instrument solves this problem by segmenting the liquid stream with bubbles. The theory is that mixing of each liquid droplet can be made quite thorough while minimizing sample spreading with the gas bubbles separating the individual droplets. However, such solution is not ideal for sample spreading remains enough to limit the rate at which sequential samples can be introduced. Additionally, debubblers must be incorporated into the system to remove any gas bubbles prior to introducing the sample to the detection means. Furthermore, the schemes here referred to require pumping of several liquid and/or gas streams at precise ratios.

Ruzicka et al (See Analytica Chimica Acta 79 145, 79; 81, 371, 387; 82, 137; 87, 353; and 88, 1) above noted have shown that it is possible to design an instrument which does not require segmentation by gas bubbles. Ruzicka refers to his scheme as "Flow Injection Analysis" primarily because his samples are injected into a reagent stream rather than being pumped as in a scheme previously described. However, Ruzicka's scheme still involves multiple stream pumping and sample spreading remains a significant problem.

As distinguished from the prior art, the present invention provides a method and apparatus for the continuous or sequential titration of process stream samples by use of a conventional chromatograhic analysis means and, also according to the invention of an electronic detection means, for determining the start point and end point of a detected titrant vacancy section occuring in a chromatograph column effluent.

Thus, the present invention provides a continuous or sequential chemical analysis of process stream samples using a packed tube, e.g., a chromatographic analysis column, as a mixing chamber for selected reagents and samples with minimal sample spreading therein.

Thus, in an embodiment of the invention, FIG. 1, sample concentration of a fluid stream is determined on a continual basis by measuring the time, under a known and constant flow rate condition, between the starting point and the end point of a reaction or titration conducted within a chromatographic column.

A titrant is supplied to two parallel fluid conducting circuits. A first circuit, comprising a pressure regulator means and a flow restricting means, terminates in a first electrical conductivity detection cell means having a vent means. A second circuit, comprising a flow rate controller means, a sample valve means and a chromatograph column or equivalent means, terminates in a second electrical conductivity detection cell means also having a vent means. The electrical output signals, respectively representative of the electrical conductivity of the fluid conducted through the first cell means and the second cell means, are combined in an electrical difference detection means. The electrical output signal, generated within said detection means and representative of the difference in said fluid conductivities, is passed to one channel of a dual channel strip chart recording means and is additionally passed to an electrical signal derivative detection means. The electrical output signal from said derivative detection means, representative of the derivative of said difference signal, is passed to the enabling input of a digital clock and counter means and is additionally passed to a second channel of said recording means.

The material or sample to be reacted or titrated is supplied to and through the sample valve via a third conduit or means.

The sample valve or equivalent is so constructed and arranged that the neatly defined, metered amount of reactant or sample or other material can be interposed into the flow which at other times is passing through the sample valve on its way to the chromatographic column.

In operation, under steady state conditions, titrant is flowing in each of the cells resulting in a "zero" signal from said difference detection means, from said derivative detection means, and said counter means. Under automatic programmer control, the sample valve is actuated periodically to result in a metered slug of a sample which is injected into said titrant stream upstream from the column. The inventive ionic exchange reaction between the titrant and the sample will take place in the column. This will result in two output signals from said derivative detection means which in turn will cause starting and stopping of the counter. The indicated count will be directly proportional to the quantity of titrant reacted with the sample.

In another embodiment, a packed tube, e.g., a chromatograph column, is utilized as a mixing chamber for providing continual or sequential chemical analysis of process streams or the like wherein a suitable reagent is retained sufficiently on a selected column packing material for subsequent reaction with a predetermined amount of injected sample. The resultant reaction products are thence passed to a suitable detector for determination of a specific component or components therein.

In a now preferred form of the invention, a solvent (carrier) is provided continuously to a sample valve means, thence to a suitable detection means, and thence to vent. A reagent and sample are provided to said valve which, under programmer control, is periodically or otherwise actuated to effect first an injection of the reagent into the solvent stream followed by an injection of the sample into said solvent stream. The packing is of such a nature that the reagent is retained thereon for a time sufficient to allow overtaking thereof by the sample. The reagent and the sample react in the packing of the column to provide a reaction product not retained by said packing material and which is passed on to and into said detection means. An electrical signal, quantitatively representative of the component or components present, is provided to a suitable recording means which in turn provides a chromatographic representation of the signal, the obtained signal is "boxcar" shaped. The vertical displacement of the recording made with aid of the signal from an arbitrary reference datum is directly proportional to the concentration of said reaction product, hence, sample.

Referring to FIG. 1, titrant from 1 is passed by pump 3 in part to flow controller 9 and in part to pressure regulator 5. Pressure regulated titrant from regulator 5 is passed to flow restrictor 7, thence to the reference cell 29 of the conductivity cell 15 via Teflon ® tubing 31, thence to waste vent line 33, also of Teflon construction. Additionally, during the initial operative phase, titrant, under constant flow condition, is passed to and through sample valve 11, thence to column 13, thence via Teflon tube 37 to sample cell 27 of conductivity cell 15 thence to waste vent via Teflon tube 35.

At this time, the conductivities of ref. cell 29 and sample cell 27 are identical and equal to the conductivity of the titrant e.g., in the example, sodium hydroxide. Conductivity detector 17 senses such conductivity and provides an electrical signal 43 representative thereof. Signal 43 is further connected to a derivative determining circuit 19 and to a first recording channel of strip chart recorder 23.

At this time, the signal 43 recorded vs. time on the chart is represented by a smooth horizontal line on the first channel. Circuit 19 derives the first derivative of signal 43 and passes an electrical signal 45 representative of it to a second recording channel of recorder 23 and to timer 21. The second channel recording, at this time, will also be a straight line; for signal 43 is a constant.

During the second operative phase of the method of the invention, sample valve 11 is actuated, as by hand, but obviously preferably is automatically operated, as under or by a programmer, to quickly or abruptly stop the flow of titrant 39 and to equally quickly admit flow of sample (in this instance, HCl), to and through sample valve 11 thence to column 13. Sample valve 11 meters the quantity of sample admitted to column 13. Valve 11 can be one as disclosed in U.S. Pat. No. 3,633,426. Thus a metered slug of sample is interposed in the broken or divided stream of titrant under constant flow conditions. Following interpositioning of the sample slug, flow of titrant is resumed. As the slug of HCl passes through column 13, the sodium ion on the resin is exchanged for hydrogen ion from the sample and as NaCl solution emerges from the column.

As the conductivity of NaCl is greater than that of NaOH, at the existing concentration levels, signal 43 increases positively. Such increased conductivity is manifested first by the smaller of two blips shown on the lower recording in FIG. 3 (the lower recording is inverted, i.e. a positive increase is shown by a dip in the curve and vice versa) and second by the very steep slope of the derivative curve shown in the upper recording. Such first steep-sloped derivative signal 45 triggers counter (timer) 21 to start counting pulses generated by its own internal clock means.

Flow of NaOH is resumed following immediately behind the slug of HCl completing its flow into column 13. As the water thus formed passes through sample cell 27, signal 43 is decreased to a minimum valve for the conductivity of water under the cell conditions is nil. At this time, signal 45 turns positive as signal 43 becomes more negative. Positive excursions of signal 45 have no effect in triggering counter 21. Signal 43 remains negative until such time as the slug of water clears the sample cell and NaOH has resumed flowing therein; at which time, signal 43 abruptly becomes positive and the derivative signal 45 turns negative, causing counter 21 to stop counting.

Thus, counter 21 is started at the instant the NaCl enters sample cell 27 and is stopped the instant NaOH enters sample cell 27. The digital count displayed by counter 21 is therefore indicative of the elapsed time between start of the NaCl slug and the end of the $H_2O$ slug. Thus it can be seen that such elapsed time, assuming a constant flow rate, is directly proportional to the total volume of "titrant vacancy" which includes the ($H_2O$) volume plus sample (NaCl) volume. Therefore, to determine the volume of titrant, it is necessary to reduce such total volume by the known (metered) volume of sample.

The principal apparatus components of FIG. 1 are identified as to function and source of supply as may be helpful to one skilled in the art in possession of this disclosure and having studied the same.

| ITEM | |
|---|---|
| 3, pump | Haskel Engineering & Supply |
| | 100 E. Graham Pl. |
| | Burbank, Ca. 91502 |
| | Model MCP-36 |
| 5, pressure regulator, | Instrument Div. |
| Veriflo Corp. | 250 Canal Blvd. |
| | Richmond, Ca. 94804 |
| | Model IR 503 R |
| 9, Flow Controller, | Model LC 221 |
| Veriflo Corp. | |
| 11, Sample valve, | Pawhuska Rd. |
| Applied Automation Inc. | Bartlesville, OK 74004 |
| | Model VIII (U.S. 3,140,615) |
| 7, Restrictor | 5 ft. of 0.0005 inch O.D. |
| | Capillary tubing |
| 13, Column | 6 inches of ⅛ inch × 0.020 inch |
| | wall tubing packed with pellionex$^c$ |
| | HCSCX resin. |
| 15, Conductivity Cell, | Div. of Milton Roy Co. |
| Laboratory Data Control | P.O. Box 10235 |
| | Riviera Beach, FL 33404 |
| | Model LDC |
| 17, Conductivity Detector, | 19414 Londelius St. |

| -continued | |
|---|---|
| ITEM | |
| Validyne Engineering Corp. | Northridge, CA 91324 |
| | Model DC15 |
| 21, Multifunction Counter, | Audubon Rd. |
| Data Precision Corp. | Wakefield, MA 01880 |
| | Model 5740 |
| 23, Strip Chart Recorder, | 1501 Page Mill Rd. |
| Hewlett-Packard Co. | Palo Alto, CA 94304 |
| | Model HP7702 B |

All tubing used was 1/16 stainless steel except those lines connecting item 15 to item 13 and item 7 and the vent lines from item 15 to waste which were of polytetrafluorethylene, Teflon. All lines were made as short as possible.

For the experimental procedure, a calibrated syringe 25 was used to manually inject a quantity of sample into sample valve 11 which in turn was manually controlled to effect the desired flow.

The circuit of FIG. 2 was constructed utilizing a model 194 circuit "manifold" 19 by Analog Devices, Inc., Rt. 1, Industrial Park, P.O. Box 280, Norwood, Mass. 02062.

Figure 3:
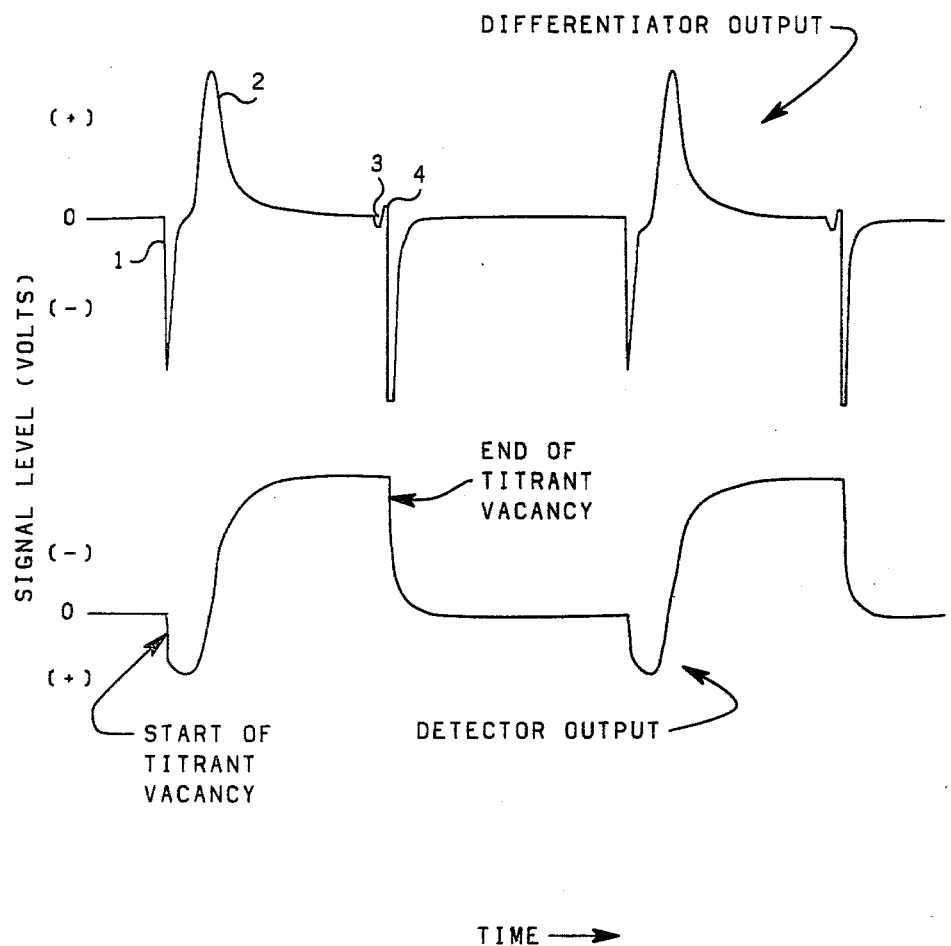
FIG. 3 represents a strip chart recording of the output of the difference detection means (lower recording) and of the output of the differentiator circuit means (upper recording) which is the derivative of the output of the difference means.

Referring now to FIGS. 2 and 3, the amplifiers (A1 through A4) and the comparator (350B) on the 194 "manifold" used as a breadboard were obtained from Analog Devices.

In operation, the detector signal is applied to A1 which is used as an approximate differentiator. The signal from A1 is inverted by A2. A3 is used to buffer the signal from A2. The signal from A3 is applied to the 350B comparator. The comparator is designed so the output will be in one of two states (high or low) depending on the input voltage. A bias is applied to the comparator by the 10K OHM divider. This is adjusted so the comparator will switch states on slopes 1 and 4 and not on slopes 2 and 3, see FIG. 3. Hysteresis is added to the comparator by the 500K OHM and the 10K OHM resistors. This reduces the likelihood of a noise switching of the comparator after slopes 1 and 4.

A CD4013 connected as a D flip-flop is switched by the comparator signal. The signal from the flip-flop is buffered by amplifier A4. The output from A4 may be used for a counter hold line. A momentary signal is applied to the comparator by a switch from the + or −15 V supply through the 100K OHM resistors. This sets the D flip-flop to the desired starting state.

By applying a signal of known frequency to the counter, gating the counter, and using the counter hold line signal as a gate, a timer is formed. The time interval measured is linearly related to the sample concentration.

As evident from the foregoing, the invention provides apparatus for analyzing, repeatedly, samples from a process stream the apparatus comprising a reagent or titrant supply means, sample supply means, means for receiving and holding one of the reagent and sample until both have been supplied to said means for receiving and holding and have had opportunity to completely react therein, the apparatus in its now preferred form having also a flow control means alternately supplying reagent and sample to said holding means and means for detecting a difference in the property, e.g. conductivity, of the effluent from said holding means; also in the now preferred form, there being means to record a signal representative of change or difference in the property measured and doing so while the difference is existing.

EXAMPLE

A column containing the sodium form of a cation exchange resin, titrant 0.010 M NaOH at a flow rate of 1 ml/min. and dilute HCl solution samples were used. The titration determined the acid content of the sample by measuring the time (hence, the volume) of the $OH^-$ vacancy in the titrant. A conductance detector was used. Precision of the analysis averaged about ±0.1% relative. Flow rate of the titrant was controlled to substantially 1 ml/min.

The titration time is determined automatically by starting and stopping a timer with the sharp negative peaks on the derivative curve. At constant flow rate, the concentration of acid in the sample is directly proportional to this time. For this particular test, the sample was 0.05 M HCl, the sample taken was 320 μl and the titration was about 110 seconds. Repetitive samples could be run on a 3-minute cycle.

The titration reaction is represented by the equation

|  | sS + tT |  | products |
|---|---|---|---|
| where | S | = | sample mols, |
|  | T | = | titrant mols. | and s & t are the coefficients of the balanced equation (in our case, 1 respectively)

| then, if | $s + t =$ mols of S | $=$ | $\frac{s}{t}$ T (mols of titrant) |
|---|---|---|---|
| then, the mols of | mols of S | = | mols of T |
| and | mols of T | = | $C_T V_T$, |
| where | $C_T$ | = | concentration of titrant (mols/liter) |
| and |  | $V_T$ = | volume of titrant. |
| The volume of the titrant has been determined to be | | | |
| | $V_T$ | = | $V_v - V_S$ | where $V_v$ is equal to the total of H₂O plus NaCl as determined above and $V_S$ is the metered quantity of sample.

| Total volume, | | |
|---|---|---|
| $V_v$ | = | flow rate (given) × time (given) |
| | = | 1 ml/min × 110 sec. |
| | = | 0.0166 ml/sec × 110 sec. |
| | = | 1.833 ml. |
| and $V_s$ (given) | = | 320μl. |
| | = | 0.320 ml. |
| Therefore, the volume of titrant | | |
| used is $V_T$ | = | 1.833 ml–0.320 ml. |
| | = | 1.513 ml. |
| Concentration of titrant is | | |
| given as $C_T$ | = | 0.01 mols/liter |
| | = | $0.01 \times 10^{-3}$ mols/ml. |
| therefore, | | |
| mols of S | = | 1.513 ml × 0.01 × 10⁻³ mols/ml |
| | = | $1.513 \times 10^{-5}$ mols. |
| and the molarity of S | = | mols of $S/V_s$ (liters) |
| | = | $1.513 \times 10^{-5}$ mols/320 × 10⁻⁶ liters |
| | = | 0.0473 mols/liter | which is approximately −5.4% of the given molarity of sample, 0.05 M absolute.

In analytical terms, the above error is recognized to be fairly large and is probably due primarily to inaccuracies of the apparatus in the breadboard set up (e.g. diffusion, sample metering, etc.) but with optimization this error can be greatly reduced, as one skilled in the art in possession of this disclosure will recognize readily.

Figure 4:
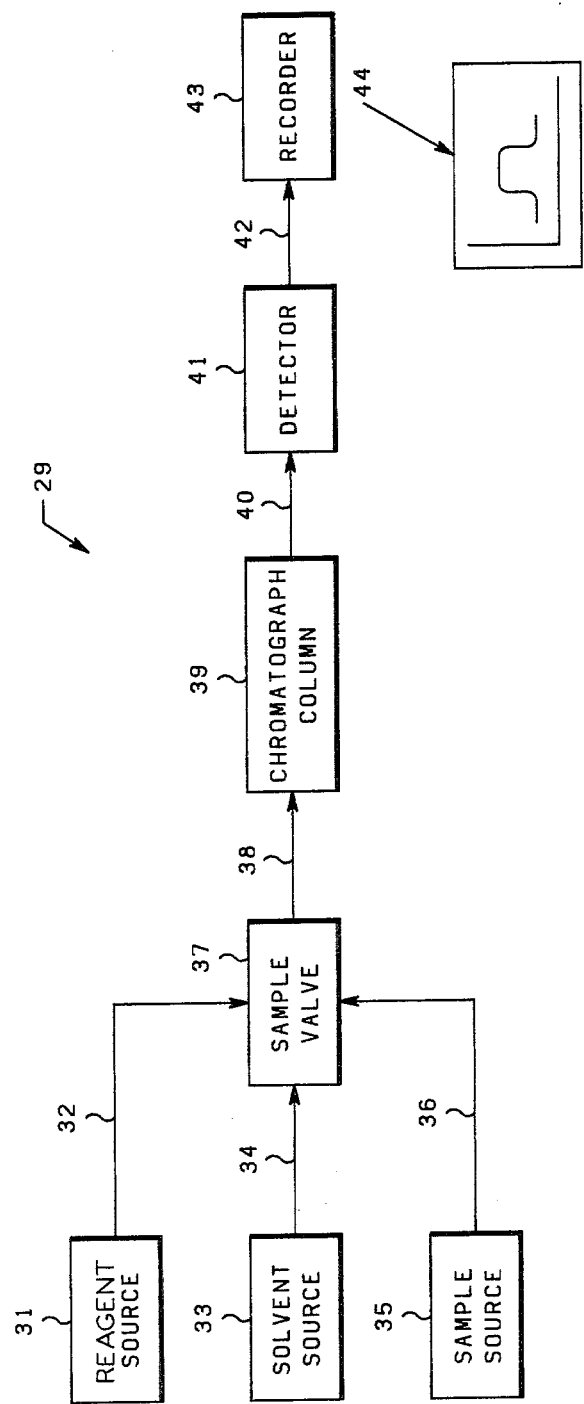
FIG. 4 is a block diagram and schematically shows interconnection of various components which operatively make up the continuous chemical analysis means of the present invention.

Referring to FIG. 4, a suitable reagent, a carrier solvent and a selected sample are provided respectively from well known sourcing means 31, 33, and 35 to a sample valve 37, e.g. that disclosed in earlier noted U.S. Pat. No. 3,633,426, via conduits 32, 34 and 36 respectively. The output of sample valve 37 is passed to a chromatograph column 39, e.g. column 13 of FIG. 1, packed with a conventional "reverse phase" packing of an aromatic hydrocarbon bonded to silica. The column 39 effluent is then passed to a detector 41, e.g. Applied Automation, Inc.'s (Bartlesville, Okla.) Model 420 Optical Absorbance Detector. The electrical signal output of detector means 41 is connected to recorder means 43 which may be identical to recorder means 23 shown on FIG. 1. A typical recording of signal 42, of, say, an example of the embodiment of the invention described here is given hereinafter, is simulated at 44.

To illustrate the just-described embodiment of this invention, a typical procedure for the method thereof is now presented: Very low concentrations of ferrous iron can be determined by reaction with orthophenanthroline (Ophen) to form an intensely colored complex:

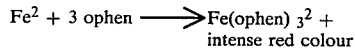

$$Fe^2 + 3\ ophen \longrightarrow Fe(ophen)_3^2 +$$
intense red colour

For this determination, a very dilute solution of ophen in water is formed and caused to flow continuously or intermittently through column 39. The preferred method is the continuous flow of said solution through column 39. Said column packing will dissolve a substantial amount of ophen from the aqueous phase until equilibrium is reached. The Fe²⁺-containing sample is now injected via sample valve 37. The sample picks up the ophen from the static phase to result in the formation of the colored complex Fe(ophen)₃²⁺. The concentration of said complex is equal (in molarity) to the molarity of Fe²⁺ in the original sample. Upon further flow of the carrier through the column, the "boxcar" shaped region containing said complex will be eluted therefrom and be passed to detector 41. The electrical output of detector 41 is directly proportional to the concentration of Fe(ophen)₃²⁺ and therefore also proportional to the concentration of Fe(ophen)₃²⁺ and therefore also proportional to the Fe²⁺ concentration in said original sample. During said elution process, the ophen removed from said static phase by the sample will be replenished from said carrier stream to thus result in the preparation of the column for receiving subsequently injected samples. In this method, the volume of sample taken is unimportant; the concentration determination is based on the height or signal level of the boxcar presentation as at 44.

Reasonable variation and modification are possible in the scope of the foregoing disclosure, the drawing, and the appended claims to the invention the essence of which is that there have been provided method and apparatus, all as described, for effecting a repeated chemical analysis of a process stream; the method comprising causing in a holding zone or column the presence of one of a reactant or sample and then injecting, in one embodiment, the other of said reactant or sample, not earlier placed into said column, to cause therein a reaction; in another embodiment simply injecting into said column, one of said reactant and sample, said one being that not already in the column; in either of the embodiments detecting and measuring and recording a graph yielding, ultimately, the desired analysis.

We claim:

1. A method for effecting a repeated chemical analysis of a process stream which comprises establishing a first flow of a stream of a first reactant into a reaction zone, retaining in said zone first reactant entering said zone, continuing said first flow until there is established in said zone a quantity of first reactant sufficient to effect in said zone a reaction therewith and with a second reactant when the latter has entered said zone, then momentarily discontinuing said first flow and simultaneously initiating a second flow of a predetermined quantity of said second reactant into said zone, then immediately upon the termination of said second flow recommencing said first flow, removing reaction product from said reaction zone, and determining at least one of the amount of and nature of reaction product thus formed and removed from said zone.

2. A method according to claim 1 wherein said first flow is of a reagent and a sample to be analyzed constitutes said second reactant.

3. A method according to claim 2 wherein at least one of the reagent and sample is aided in its flow with a solvent or diluent.

4. A method according to claim 1 wherein the reaction product is used to alter a signal from a photometer.

5. A method according to claim 1 wherein the reaction product is used to alter a signal from a conductivity cell.

6. A method according to claim 1 wherein a property of said reaction product is determined for a period of time in an analyzing zone emitting a signal representative of said first reactant when it alone is in said analyzing zone and of said reaction product when it is in said analyzing zone, a second stream of said first reactant is passed into a parallel analyzing zone emitting a signal representative of said first reactant, and wherein the signals received from the analyzing zones are compared and recorded with respect to time.

7. A method according to claim 6 wherein the property of said reaction product is a physical property.

8. A method according to claim 6 wherein the property of said reaction product is an electrical property.

9. A method according to claim 6 wherein the conductances of said reaction product and of said first reactant are measured, each measurement producing an electrical signal, and the signals are combined to produce a final signal which is recorded together with at least the period of time during which said conductances are being measured.

10. A method according to claim 1 wherein said second reactant is a sample, a first stream of said first reactant is continuously caused to flow into and through a reference conductivity cell, a second stream of said first reactant is caused to flow into a chromatographic or equivalent column or zone adapted to retain said first reactant until it is reacted with a known amount of said sample, flow of said second stream of said first reactant is abruptly discontinued while simultaneously flow of said known amount of sample is abruptly initiated and substituted for a same amount of said first reactant flowing into said column or zone, flow of said second stream of said first reactant is immediately resumed after flow of said known amount of sample has been terminated, the effluent from said column or zone is caused continuously to flow to and through a second conductivity cell, the conductivities of the respective flows in said cells are determined and caused to emit signals respectively representative of the natures of the fluids in said cells, and wherein said signals are combined to yield a final signal which is recorded with respect to time elapsing during generation of said signals.

11. A method according to claim 6 wherein the time during which the signals are different is measured by detecting with a detector said different signals at least while they are different, causing a difference in said signals when it appears to initiate operation of a counter, to continue the operation of said counter for the time during which said signals are different and to stop said counter when said signals have again become constant and the same.

12. A method according to claim 11 wherein the initiating of the operation of said counter and the stopping of the operation of said counter comprises: supplying the signal or output of said detector to a first input of a comparator; supplying a reference voltage to a second input of said comparator; supplying the output signal from a comparator to a clock input of a D flip-flop; electrically connecting the data input of said D flip-flop to the $\overline{Q}$ output of said D flip-flop; and electrically connecting the $\overline{Q}$ output of said D flip-flop to a hold line of said counter means, the $\overline{Q}$ output of said D flip-flop initiating said counter when said reaction product enters said analyzing zone and the $\overline{Q}$ output of said D flip-flop stopping said counter when said reaction product has left said analyzing zone.

13. A method according to claim 12 wherein the step of supplying the output of said detector to the first input of said comparator comprises: supplying the output of said detector to the input of a differentiator; and supplying the output of said differentiator to the first input of said comparator.

14. An apparatus for effecting a repeated chemical analysis of a process stream which comprises in combination a reagent supplying means, and a sample supplying means, a means for receiving and holding one of said reagent and sample, until both are in said means for holding and have reacted therein, a flow control means adapted to alternately supply said reagent at a predetermined quantity of said sample to, into and through said holding means, means to detect a difference in a property of the effluent from said holding means when said effluent is constituted by reagent at one time and by reaction product at another, and means to record a signal representative of the change or difference in said property while said difference is extant.

15. An apparatus according to claim 14 wherein said holding means comprises a chromatographic column.

16. An apparatus according to claim 14 wherein said means to detect is a photometer.

17. An apparatus according to claim 14 wherein means are provided to supply a flow of said reagent at a predetermined rate to and through a reference conductivity cell, means are provided to flow the effluent from said holding means to and through another conductivity cell, means to provide a signal from each of said cells representative of the respective conductivities of fluid in said cells, and means to detect and to combine signals from said cells and record with respect to time elapsing the signal resulting from the combined signals.

18. An apparatus according to claim 17 wherein said holding means comprises a chromatographic column.

19. An apparatus according to claim 17 wherein means are provided responsive to said difference to initiate operation of a counter, to continue the operation of said counter for the time period during which said signals are different and to stop said counter when said signals have again become constant and the same.

20. An apparatus according to claim 19 wherein the means initiating the operation of said counter and stopping the operation of said counter comprise: a comparator and a D flip-flop, means to supply the signal or output of said detector to a first input of said comparator, means to supply a reference voltage to a second input of said comparator, means for supplying the output signal from said comparator to a clock input of said D flip-flop, electrical means connecting the data input of said D flip-flop to the $\overline{Q}$ output of said D flip-flop, means electrically connecting the $\overline{Q}$ output of said D flip-flop to a hold line of said counter means, whereby the $\overline{Q}$ output of said D flip-flop will initiate said counter when said reaction product enters said another conductivity cell and the $\overline{Q}$ output of said D flip-flop will stop said counter when said reaction product has left said another conductivity cell.

21. An apparatus according to claim 19 wherein said holding means comprises a chromatographic column.

22. An apparatus according to claim 19 wherein the means for supplying the output of said detector to the first input of said comparator comprises: means for supplying the output of said detector to the input of a differentiator and means for supplying output of said differentiator to the first input of said comparator.

23. A method for effecting a repeated chemical analysis of a process stream according to claim 1 wherein there are provided a sample valve adapted to instantly supply a reagent from a reagent source, a sample from a sample source, to instantly cut off supply of reagent from said reagent source while simultaneously supplying sample from said sample source, and vice versa, a chromatographic column, a detector, and a recorder, feeding reagent through said sample valve to said chromatographic column in a quantity sufficient to effect in said column a reaction or titration of a sample later to be fed to said column, feeding through said sample valve said sample in a metered quantity, immediately upon having fed said metered quantity reestablishing flow of said reagent through said sample valve, detecting in said detector at least one of the amount and nature of reaction product thus formed and removed from said zone.

24. A method according to claim 23 wherein said detector comprises a photocell.

25. A method according to claim 24 wherein said detector comprises a conductivity cell.

26. A method according to claim 10 wherein there are provided a titrant supply and a sample supply, a pump, a pressure regulator, a restrictor, and a reference conductivity cell and a detector, titrant supply is pumped by said pump through said pressure regulator, said restrictor and into and through said reference conductivity cell, there are also provided a flow controller, a sample valve, and said chromatographic or equivalent holding column and a sample conductivity cell, titrant is pumped by said pump through said flow controller, sample valve into said column and ultimately discharge from said column is passed through said sample conductivity cell, wherein said sample valve instantly shuts off flow of titrant and commences flow of said known amount of sample following which said sample valve instantly shuts off flow of sample and resumes flow of titrant, the conductivities of fluids in said cells are determined and processed as in claim 10.

27. A method according to claim 26 wherein there are provided a detector, a differentiator, a counter and a recorder, the signals from said conductivity cells are detected in said detector, combined and passed to said differentiator causing said differentiator to start and to stop a counter during titration and to record a titrant vacancy.

28. A method according to claim 1 wherein said second flow of a predetermined quantity of said second reactant is interposed as a neat slug into said first flow of reactant as it is flowing to, into and through said second reaction zone in a manner that the front face of said second reactant forms a sharply interface with the rear face or end of said first reactant and a similary sharply defined interface between the rear face of said slug and the front face of said first reactant as it resumes its flow at the point of interposition of said second reactant.

29. A method according to claim 10 wherein said titrant and said sample are interchanged.

* * * * *